(12) United States Patent
Xu et al.

(10) Patent No.: US 10,500,336 B2
(45) Date of Patent: Dec. 10, 2019

(54) SMART WEARABLE DEVICE, METHOD FOR IMPLEMENTING FIRST-AID BY THE SAME AND COMPUTER STORAGE MEDIUM

(71) Applicants: BOE TECHNOLOGY GROUP CO., LTD., Beijing (CN); HEFEI BOE OPTOELECTRONICS TECHNOLOGY CO., LTD., Hefei, Anhui Province (CN)

(72) Inventors: Fei Xu, Beijing (CN); Jun Hong, Beijing (CN)

(73) Assignees: BOE TECHNOLOGY GROUP CO., LTD., Beijing (CN); HEFEI BOE OPTOELECTRONICS TECHNOLOGY CO., LTD., Hefei, Anhui (CN)

( * ) Notice: Subject to any disclaimer, the term of this patent is extended or adjusted under 35 U.S.C. 154(b) by 380 days.

(21) Appl. No.: 15/528,965

(22) PCT Filed: Sep. 5, 2016

(86) PCT No.: PCT/CN2016/098054
§ 371 (c)(1),
(2) Date: May 23, 2017

(87) PCT Pub. No.: WO2017/177605
PCT Pub. Date: Oct. 19, 2017

(65) Prior Publication Data
US 2018/0185580 A1     Jul. 5, 2018

(30) Foreign Application Priority Data
Apr. 14, 2016   (CN) .......................... 2016 1 0230508

(51) Int. Cl.
*A61M 5/20*   (2006.01)
*A61B 5/024*  (2006.01)
(Continued)

(52) U.S. Cl.
CPC ........... *A61M 5/20* (2013.01); *A61B 5/02438* (2013.01); *A61B 5/746* (2013.01); *A61M 5/172* (2013.01);
(Continued)

(58) Field of Classification Search
CPC ......... A61B 5/00; A61B 5/02; A61B 5/02007; A61B 5/021; A61B 5/024; A61B 5/0255;
(Continued)

(56) References Cited

U.S. PATENT DOCUMENTS 5,800,420 A * 9/1998 Gross .................... A61K 9/0021
                                                        204/280
5,807,375 A * 9/1998 Gross .................... A61K 9/0021
                                                        600/309
(Continued)

FOREIGN PATENT DOCUMENTS

CN    202459636 U    10/2012
CN    103393411 A    11/2013
(Continued)

OTHER PUBLICATIONS

International Search Report and Written Opinion in PCT/CN2016/098054 dated Jan. 17, 2017, with English translation.
(Continued)

*Primary Examiner* — Jason E Flick
(74) *Attorney, Agent, or Firm* — Womble Bond Dickinson (US) LLP (57) ABSTRACT

The present disclosure relates to the smart wear field. The smart wearable device comprises: a main body comprising a control unit and a biological feature parameter acquisition
(Continued)

module, the biological feature parameter acquisition module is configured to acquire a monitored biological feature parameter of a user, and the control unit is configured to compare the monitored biological feature parameter and a pre-stored biological feature reference parameter so as to determine whether the user is in need of first aid according to the comparative result; a connecting part for putting on the smart wearable device on the body of the user; a power supply module for supplying power to the smart wearable device; and a first-aid processing module configured to give first aid to the user when it is determined according to the comparative result that the user is in need of first aid.

20 Claims, 6 Drawing Sheets (51) Int. Cl.
*A61B 5/00* (2006.01)
*A61M 5/172* (2006.01)
*A61M 5/32* (2006.01)

(52) U.S. Cl.
CPC ........ *A61M 5/1723* (2013.01); *A61M 5/3287* (2013.01); *A61B 5/681* (2013.01); *A61M 2205/18* (2013.01); *A61M 2205/3303* (2013.01); *A61M 2205/50* (2013.01); *A61M 2205/52* (2013.01)

(58) Field of Classification Search
CPC ....... A61B 5/68; A61B 5/6801; A61B 5/6802; A61B 5/6811; A61B 5/6813; A61B 5/6824; A61B 5/74; A61B 5/02438; A61B 5/681; A61B 5/746; A61M 2205/18; A61M 2205/3303; A61M 2205/50; A61M 2205/52; A61M 5/172; A61M 5/1723; A61M 5/20; A61M 5/3287; A61M 2205/33; A61M 2205/3327; A61M 2005/1726; A61M 5/178; A61M 2005/206
USPC .......................................................... 604/66
See application file for complete search history.

(56) References Cited

U.S. PATENT DOCUMENTS

2010/0049172 A1\* 2/2010 Chance ................ A61B 5/0059
604/890.1
2016/0135706 A1\* 5/2016 Sullivan ............... A61B 5/0059
600/301

FOREIGN PATENT DOCUMENTS

| CN | 204274498 U | 4/2015 |
| CN | 104777742 A | 7/2015 |
| CN | 105105730 A | 12/2015 |
| CN | 105342599 A | 2/2016 |
| CN | 105796086 A | 7/2016 |
| KR | 20150037004 A | 4/2015 |
| WO | WO 9614026 A1 | 5/1996 |

OTHER PUBLICATIONS

Office Action received for Chinese Patent Application No. 201610230508.X, dated Oct. 10, 2017, 15 pages (7 pages of English Translation and 8 pages of Original Document).

\* cited by examiner

light outlet

SMART WEARABLE DEVICE, METHOD FOR IMPLEMENTING FIRST-AID BY THE SAME AND COMPUTER STORAGE MEDIUM

RELATED APPLICATIONS

The present application is the U.S. national phase entry of PCT/CN2016/098054 with an International filing date of Sep. 5, 2016, which claims the benefit of Chinese Application No. 201610230508.X, filed on Apr. 14, 2016, the entire disclosures of which are incorporated herein by reference.

TECHNICAL FIELD

The present disclosure relates to the smart wear field, and more particularly to a smart wearable device, a method for implementing first-aid by means of the smart wearable device, and a computer readable storage medium.

BACKGROUND ART

As the electronic intelligence technology develops, various wearable devices emerge in succession, such as smart wristbands, smart watches and smart glasses. With the increase of market demands, higher functional requirements are set for the wearable devices. It is necessary to develop functions of wearable devices.

Current smart wearable devices can measure biological features of humans, for example, measure humans' heart rates and blood pressure. The functions of these smart wearable devices, however, are only limited to the measurement of biological features and unable to provide urgent solutions when people feel uncomfortable, so these smart wearable devices cannot meet the requirements when people are in urgent need of first-aid services.

SUMMARY

To solve or alleviate at least one of the defects in the prior art, it is desired to provide a smart wearable device, a method for implementing first-aid by means of the smart wearable device, and a computer readable storage medium, so as to give first aid to users who are in need of first aid.

According to one aspect, there is provided a smart wearable device. The smart wearable device may comprise:

a main body comprising a control unit and a biological feature parameter acquisition module, the biological feature parameter acquisition module being configured to acquire a monitored biological feature parameter of a user, and the control unit being configured to compare the monitored biological feature parameter and a pre-stored biological feature reference parameter so as to determine whether the user is in need of first aid according to the comparative result;

a connecting part for putting on the smart wearable device on the body of the user;

a power supply module for supplying power to the smart wearable device; and a first-aid processing module configured to give first aid to the user when it is determined according to the comparative result that the user is in need of first aid.

In an embodiment, the first-aid processing module is disposed on the connecting part.

In an embodiment, the first-aid processing module comprises an injection module, a needle push module and a medicine supply module. The injection module is provided at a first end with a needle and is connected at a second end with the needle push module. When it is determined that the user is in need of first aid according to the comparative result, the control unit controls the needle push module to push the second end of the injection module, so as to make the needle pierce the body of the user, and controls the medicine supply module to push the medicine into the injection module during the control of the needle push module, in such a way that the medicine is pushed into the body of the user through the needle.

In an embodiment, the needle push module comprises a first electromagnetic valve, a first push component and a hydraulic component having a cavity. The first end of the first push component is connected with the first electromagnetic valve, and the second end of the first push component is movably disposed in the first end of the cavity of the hydraulic component. The second end of the injection module is movably disposed in the second end of the cavity of the hydraulic component. The control unit sends a first instruction to the first electromagnetic valve. The first electromagnetic valve pushes the first push component according to the first instruction of the control unit, and the first push component when pushed by the first electromagnetic valve acts on the hydraulic component so that the hydraulic component pushes the second end of the injection module.

In an embodiment, when the control unit detects that the push of the medicine in the injection module is completed, the control unit sends a second instruction to the first electromagnetic valve. The first electromagnetic valve withdraws the first push component according to the second instruction of the control unit, and the first push component when withdrawn by the first electromagnetic valve acts on the hydraulic component, so that the hydraulic component withdraws the injection module.

In an embodiment, the cavity of the hydraulic component is L-shaped or U-shaped.

In an embodiment, the injection module further comprises a sealing module for sealing the end of the needle to be pierced into the body of the user.

In an embodiment, the medicine supply module comprises a second electromagnetic valve, a second push component, a medicine storage component and a medicine output component. The control unit sends a third instruction to the second electromagnetic valve. The second electromagnetic valve pushes the second push component according to the third instruction of the control unit, so that the second push component pushes the medicine in the medicine storage component and the medicine is pushed through the medicine output component into the injection module.

In an embodiment, the injection module is a hollow cylinder, and a medicine input port is disposed in the sidewall of the injection module that is close to the medicine supply module. The medicine is pushed through the medicine output component into the medicine input port and then pushed through the medicine input port into the injection module.

In an embodiment, the medicine output component is a flexible tube.

In an embodiment, the smart wearable device further comprises:

a blood vessel calibration module adhered to the body of the user and aligned with the blood vessel of the user;

a positioning module for aligning the needle of the injection module with the blood vessel calibration module so as to insert the needle into the blood vessel of the user at a predetermined angle.

In an embodiment, the smart wearable device is further provided with an alarm module for receiving a fourth instruction from the control unit when the control unit determines that the user is in need of first aid according to the comparative result, and sending alarm information according to the fourth instruction; and/or a storage module for storing the biological feature reference parameter.

In an embodiment, the main body further comprises a display module configured to display the monitored biological feature parameter.

In an embodiment, the monitored biological feature parameter comprises a heart rate of the user.

According to another aspect, there is provided a method for implementing first-aid by means of a smart wearable device, comprising the steps of:

controlling a biological feature parameter acquisition module of the smart wearable device to acquire a monitored biological feature parameter of the user when the smart wearable device put on the body of the user is powered up;

comparing the monitored biological feature parameter and a pre-stored biological feature reference parameter; and controlling a first-aid processing module of the smart wearable device to give first aid to the user when it is determined that the user is in need of first aid according to the comparative result.

In an embodiment, the step of controlling a first-aid processing module of the smart wearable device to give first aid to the user when it is determined that the user is in need of first aid according to the comparative result further comprises the steps of:

controlling a needle push module of the first-aid processing module to push an injection module of the first-aid processing module so that the needle of the injection module pierces into the body of the user; and controlling a medicine supply module of the first-aid processing module to push the medicine into the injection module so that the medicine is pushed through the needle into the body of the user.

In an embodiment, the step of controlling a needle push module of the first-aid processing module to push an injection module of the smart device comprises the step of:

sending a first instruction to a first electromagnetic valve of the needle push module, the first electromagnetic valve pushing a first push component of the needle push module according to the first instruction, the first push component acting on a hydraulic component of the needle push module so as to make the hydraulic component to push the injection module to move.

In an embodiment, the step of controlling a medicine supply module of the first-aid processing module to push the medicine into the injection module comprises the step of:

sending a third instruction to a second electromagnetic valve of the medicine supply module, the second electromagnetic valve pushing a second push component of the medicine supply module according to the third instruction, the second push component pushing the medicine in a medicine storage component of the medicine supply module so that the medicine is pushed through a medicine output component of the medicine supply module into the injection module.

In an embodiment, the medicine is pushed through the medicine output component to a medicine input port disposed in the sidewall of the injection module that is close to the medicine supply module, and is pushed through the medicine input port into the injection module.

In an embodiment, the step of controlling a needle push module of the first-aid processing module to push an injection module of the first-aid processing module further comprises the step of:

positioning a needle of the injection module so that the needle is inserted into a blood vessel of the user at a predetermined angle.

In an embodiment, the method further comprises the step of:

when detecting that the push of the medicine in the injection module is completed, sending a second instruction to the first electromagnetic valve, the first electromagnetic valve withdrawing the first push component according to the second instruction, and the first push component when withdrawn by the first electromagnetic valve acting on the hydraulic component so that the hydraulic component withdraws a second end of the injection module.

In an embodiment, the method further comprises any combination of the following steps:

sending a fourth instruction to an alarm module of the smart wearable device so that the alarm module sends alarm information according to the fourth instruction;

sending a fifth instruction to a display module of the smart wearable device so that the display module displays the monitored biological feature parameter according to the fifth instruction.

In an embodiment, the monitored biological feature parameter comprises a heart rate of the user.

According to another aspect, there is provided a computer readable storage medium containing computer executable instructions thereon which, when executed by one or more processors, cause the one or more processors to execute any one of the above methods.

The embodiments of the present disclosure can realize at least one of the following advantageous effect and/or other advantageous effect:

When the smart wearable device is powered up, the control unit can determine whether the user is in need of first aid according to the acquired monitored biological feature parameter. If the user needs first-aid services, the user can be injected with the medicine by the first-aid processing module in the smart wearable device. Thus, the embodiments of the present disclosure can give first aid to users when they are in need of first aid.

BRIEF DESCRIPTION OF DRAWINGS

To explain the technical solutions in the embodiments more clearly, the drawings to be used in the Detailed Description will be briefly introduced below. It should be realized that the following drawings are only related to some embodiments of the present invention. Those skilled in the art can obtain other drawings that fall within the scope of the present invention according to these drawings without making an inventive labour.

DETAILED DESCRIPTION

To assist those skilled in the art in better understanding the object, technical solutions and advantages of some embodiments, the embodiments will be further described in detail with reference to the drawings and detailed description. The following embodiments are used to explain the present invention, but not used to limit the scope of the present invention.

Figure 1:
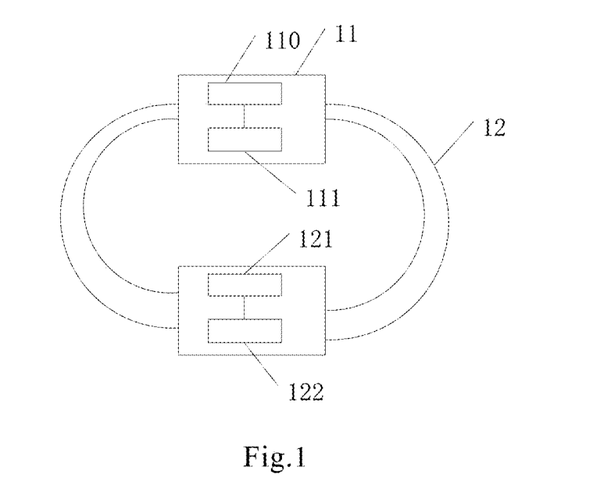
FIG. 1 is a first schematic view of a smart wearable device according to an embodiment.

FIG. 1 is a first schematic view of a smart wearable device according to an embodiment. As shown in FIG. 1, the smart wearable device may comprise a main body 11 and a connecting part 12. The main body 11 may comprise a control unit 110 and a biological feature parameter acquisition module 111, wherein the control unit 110 may be a central processing unit, a microprocessor or any other unit having computing capability. The connecting part 12 can be used to put the smart wearable device on the body of the user. As shown, the smart wearable device may also comprise a first-aid processing module 121 and a power supply module 122. The first-aid processing module 121 can be disposed on the connecting part 12 as shown in FIG. 1. The power supply module 122 is used to supply power to the smart wearable device. The power supply module 122 can be disposed on the connecting part 12 as shown in FIG. 1. Of course, the first-aid processing module 121 and the power supply module 122 can be disposed in other position of the main body (not shown).

When the smart wearable device is powered up, the biological feature parameter acquisition module 111 can be configured to acquire a monitored biological feature parameter of the user. The biological feature parameter acquisition module 111 can also send the monitored biological feature parameter as acquired to the control unit 110. In an embodiment, the acquisition and the sending are conducted under the control of the control unit 110. To be specific, the control unit 110 may send an instruction to the biological feature parameter acquisition module 111 for instructing the biological feature parameter acquisition module 111 to acquire the monitored biological feature parameter of the user. Then, the biological feature parameter acquisition module 111 sends to the control unit 110 a response message which carries the acquired monitored biological feature parameter of the user.

Then, the control unit 110 compares the monitored biological feature parameter with the pre-stored biological feature reference parameter. When it is determined that the user is in need of first aid according to the comparative result, the first-aid processing module 121 can be configured to give first aid to the user. In an embodiment, the first-aid processing module 121 gives first aid under the control of the control unit 110.

As can be seen, after the smart wearable device is powered up, the control unit can determine whether the user is in need of first aid according to the monitored biological feature parameter as acquired. If the user is in need of first aid, then the first-aid processing module in the smart wearable device is used to inject the medicine into the user. In this way, the users can be given first aid when they are in need of first aid due to their physical conditions.

The structure and working principle of the first-aid processing module will be described with reference to the corresponding drawings below.

Figure 2:
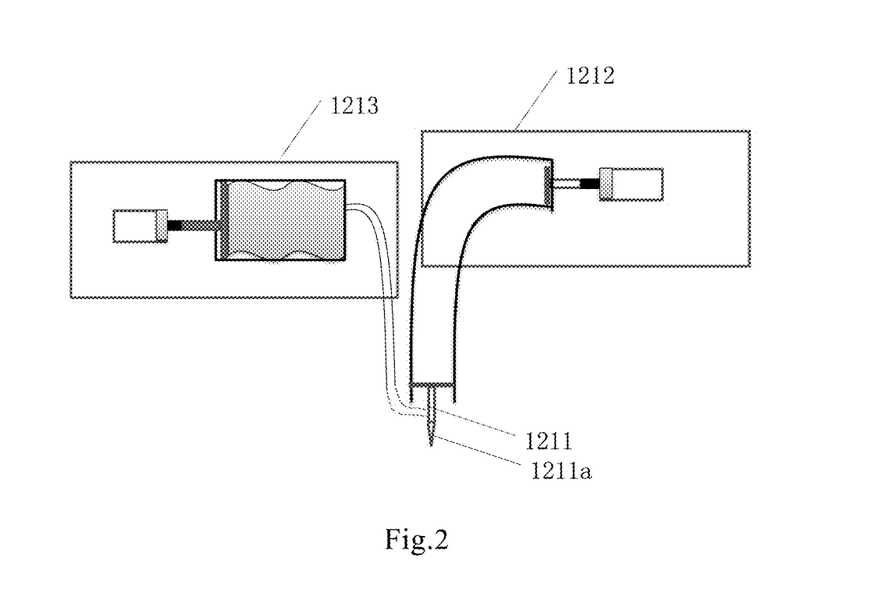
FIG. 2 is a first schematic view of a first-aid processing module according to an embodiment.

FIG. 2 is a first schematic view of the first-aid processing module according to an embodiment. As shown in FIG. 2, the first-aid processing module comprises an injection module 1211, a needle push module 1212 and a medicine supply module 1213. The injection module 1211 is provided at a first end with a needle 1211a and is connected at a second end with the needle push module 1212.

In some embodiments, to guarantee the safety of pharmaceutical use, a sealing module is disposed at the end of the needle 1211a to be pierced into the body of the user (not shown in FIG. 2). The sealing module may be a rubber tube with one end sealed and the other end sleeved onto the needle, and it shall be ensured that the rubber tube is not pierced by the needle before use.

In some embodiments, the biological feature parameter acquisition module may be a photoelectrical detecting module. The smart wearable device can be worn on, e.g. the wrist of the user.

Take the smart wearable device on the wrist of the user as an example. During the process of wearing the smart wearable device by the user, when the smart wearable device is powered up, the control unit 110 can control the photoelectrical detecting module 111 to acquire the monitored biological feature parameter of the user, and obtain the monitored biological feature parameter from the photoelectrical detecting module 111. To be specific, the photoelectrical detecting module emits detecting light through a light outlet disposed at a side close to the wrist of the user and receives the reflective light from the wrist, and then determines the monitored biological feature parameter of the user according to the reflective light.

Then, the control unit 110 may compare the monitored biological feature parameter with the pre-stored biological feature reference parameter. In some embodiments, the monitored biological feature parameter refers to a heart rate value of the user. Correspondingly, the biological feature reference parameter refers to a heart rate reference value.

The heart rate reference value may be a heart rate value that right indicates that the user does not need first aid. For instance, in a specific application, the heart rate of the user can be monitored periodically within a certain period of time. For instance, within a week, the heart rate of the user is monitored periodically every two hours each day. Among the acquired multiple heart rate values, the minimum heart rate value serves as the heart rate reference value and is stored.

The control unit 110 receives the monitored heart rate value acquired by the biological feature parameter acquisition module, and converts the format of the monitored heart rate value so as to be compared with the pre-stored heart rate reference value. If the monitored heart rate value is smaller than the heart rate reference value, it is deemed that the user needs first aid; otherwise, it is deemed that the user does not need first aid. Of course, in some embodiments, other parameter may serve as the monitored biological feature parameter, such as the blood oxygen condition. The corresponding biological feature reference parameter may also be the blood oxygen condition which indicates that the user's body just does not need first aid.

When it is determined that the user is in need of first aid according to the comparative result, the control unit 110 controls the needle push module 1212 to push the second end of the injection module 1211, so as to make the needle 1211a pierce the body of the user, and controls the medicine supply module 1213 to push the medicine into the injection module 1211 during the control of the needle push module 1212, in such a way that the medicine is pushed into the body of the user through the needle 1211a. What is stored in the medicine supply module is the medicine for giving first aid to the user.

Figure 3:
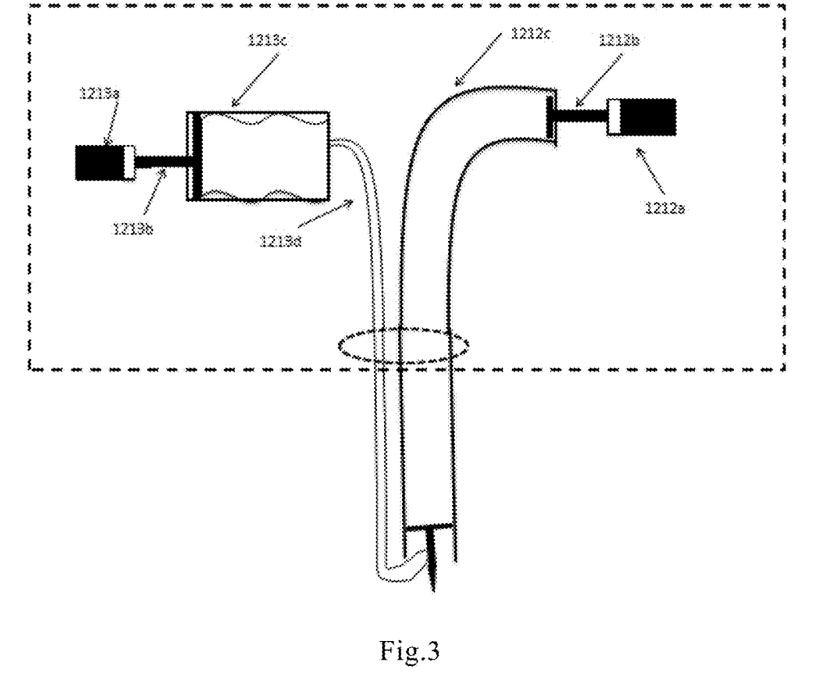
FIG. 3 is a second schematic view of a first-aid processing module according to an embodiment.
Figure 4:
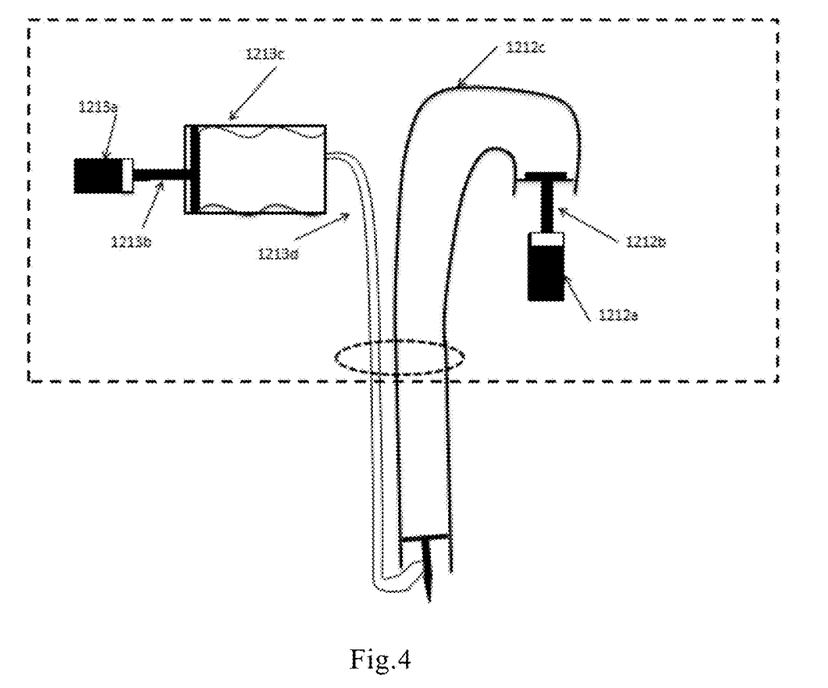
FIG. 4 is a third schematic view of a first-aid processing module according to an embodiment.

FIG. 3 is a second schematic view of a first-aid processing module according to an embodiment. As shown in FIG. 3, the needle push module 1212 may comprise a first electromagnetic valve 1212a, a first push component 1212b and a hydraulic component 1212c having a cavity. In FIG. 3, the cavity of the hydraulic component is L-shaped. Or, as shown in FIG. 4, the cavity of the hydraulic component may also be U-shaped. Through such a design, the thickness of the first-aid processing module can be reduced, thereby decreasing the thickness of the connecting part to make the smart wearable device more comfortable. The first push component 1212b in some embodiments may be a push rod.

In FIG. 3, the first end of the first push component 1212b is connected with the first electromagnetic valve 1212a, and the second end of the first push component 1212b is movably disposed in the first end of the cavity of the hydraulic component 1212c. The second end (the end with no needle) of the injection module is movably disposed in the second end of the cavity of the hydraulic component 1212c.

In FIG. 3, the medicine supply module 1213 may comprise a second electromagnetic valve 1213a, a second push component 1213b, a medicine storage component 1213c and a medicine output component 1213d. The second push component 1213b in some embodiments may be a push rod.

When the control unit 110 determines that the user is in need of first aid, a first instruction is sent to the first electromagnetic valve 1212a to notify the first electromagnetic valve 1212a to operate. At this time, the first electromagnetic valve 1212a generates an electromagnetic force according to the first instruction of the control unit. The first push component 1212b is pushed to move under the action of the electromagnetic force. Furthermore, the first push component 1212b when pushed by the first electromagnetic valve 1212a acts on the hydraulic component 1212c so that the hydraulic component 1212c pushes the second end of the injection module to move.

At the beginning of the operation, the current of the first electromagnetic valve 1212a increases gradually from zero. When the needle pierces out of the rubber tube, the load gets smaller, and the current of the first electromagnetic valve 1212a leaps (a first leap) from large to small. When the needle pierces the skin, the load gets larger, and the current of the first electromagnetic valve 1212a leaps (a second leap) from small to large. When the needle pierces the blood vessel, the load becomes smaller again, and the current of the first electromagnetic valve 1212a again leaps (a third leap) from large to small. When the current of the first electromagnetic valve 1212a leaps for three times, the control unit switches off the first electromagnetic valve 1212a for a preset time so that the first electromagnetic valve 1212a does not operate any longer and the needle is never pushed, so as to ensure that the needle does not pierce through the blood vessel.

The preset time is obtained through the following manner:

$$t \times u = l$$

Wherein t indicates the preset time, u indicates the theoretical moving velocity of the needle, and l indicates the theoretical length that the needle can pierce the blood vessel, and wherein l and u can be preset.

After the first electromagnetic valve 1212a works for a period of time, the second electromagnetic valve 1213a pushes the second push component 1213b according to the third instruction of the control unit 110, so that the second push component 1213b pushes the medicine in the medicine storage component 1213c and the medicine is pushed through the medicine output component 1213d into the injection module.

In an embodiment, the second push component 1213b can push the medicine in the medicine storage component 1213c at a uniform speed. The control unit can control the relationship between the speed of pushing the hydraulic component by the first push component and the speed of pushing the medicine in the medicine storage component by the second push component, e.g., they can be controlled to be the same. In some embodiments, it takes certain time for the needle push module to push the injection module to move, so a third instruction is sent to the second electromagnetic valve at some delayed time after the control unit sends the first instruction. The delayed time can be set as required, e.g., 50 ms.

In some embodiments, the pushing speed of the second push component can be determined according to the following manner:

$$u_2 = u_1 \times s_1 / s_2$$

Wherein $u_2$ is the push speed of the second push component (unit: m/s), $u_1$ is a fluid flow rate within the needle (unit: m/s), $s_1$ is the cross-sectional area of the medicine storage component 1213c (unit: $m^2$), and $s_2$ is the cross-sectional area of the needle (unit: $m^2$).

Thus, the speed v of injecting the medicine of the medicine storage component 1213c is $v = s_2 \times u_2$ (unit: $m^3$/s).

In some embodiments, the injection module is a hollow cylinder, and a medicine input port is disposed in the sidewall of the injection module that is close to the medicine supply module. Then, the medicine is pushed through the medicine output component into the medicine input port and then pushed through the medicine input port into the injection module. If the injection module is not provided with a medicine input port, then, in the embodiment, the end of the medicine output port that is in contact with the injection module may be provided with a pointed portion which may pierce the sidewall of the injection module so as to push the medicine into the injection module. Then, correspondingly, the sidewall of the injection module needs to be made of a material that can be pierced by the pointed portion. Or, the medicine output component can be integrally formed with the injection module. To guarantee the normal feeding of the medicine, the medicine output component may be made of a flexible tube.

The medicine storage component can store a medicine dose for one time of first aid, or a medicine dose for multiple times of first aid. No matter how many stored medicine doses there are, the pushed speed and dose of the pushed medicine can be controlled according to such factors as volume or size of the medicine storage component according to a certain algorithm so as to satisfy the first-aid needs.

FIG. 4 is a third schematic view of a first-aid processing module according to an embodiment. FIG. 4 shows another form of the cavity of the hydraulic component. As shown, the cavity of the hydraulic component is U-shaped. Other components in FIG. 4 are the same as those in FIGS. 2 and 3 in terms of structure and function, which will not be reiterated. In FIGS. 3 and 4, for easy operation, the hydraulic component may be made in the form of a hydraulic hose.

Figure 5:
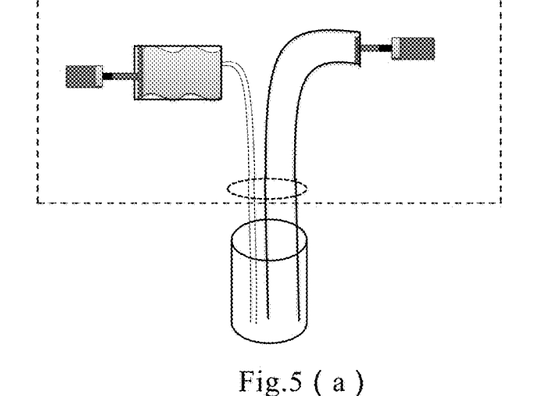
FIG. 5(a) is a fourth schematic view of a first-aid processing module according to an embodiment.
FIG. 5(b) is a fifth schematic view of a first-aid processing module according to an embodiment.

FIGS. 5(a) and 5(b) are respectively a fourth and a fifth schematic view of a first-aid processing module according to an embodiment. As shown in FIG. 5(a) or 5(b), in a specific application, the needle may be fixed for easy use. When in use, a portion of the hydraulic hose of the hydraulic component, the needle and a portion of the medicine output component can be together arranged into a hermetic fixed structure.

Figure 6:
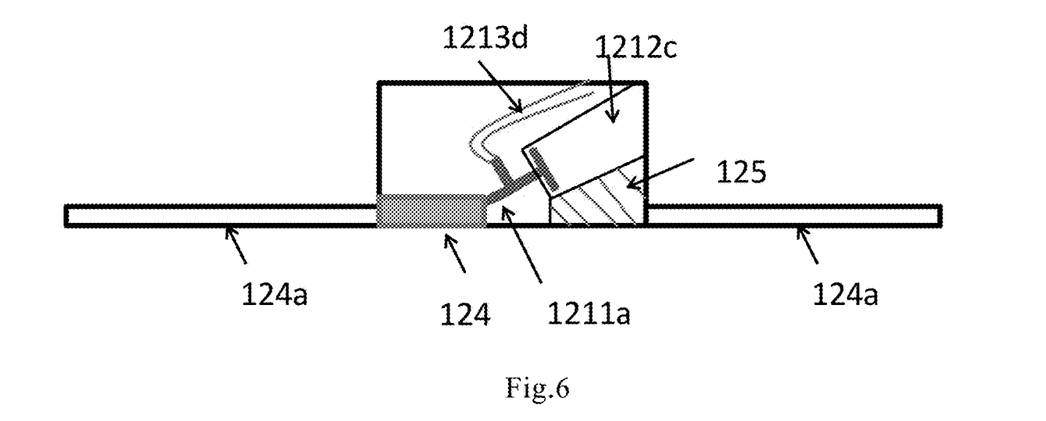
FIG. 6 is a schematic view of a fixing structure of the smart wearable device according to an embodiment.

FIG. 6 is a schematic view of a fixing structure of the smart wearable device according to an embodiment. As shown in FIG. 6, in the fixed structure, the smart wearable device may further comprise a blood vessel calibration module 124 that can be adhered to the body of the user e.g. by an adhesive 124a and aligned with the blood vessel of the user; a positioning module 125 for aligning the needle of the injection module with the blood vessel of the user so as to insert the needle into the blood vessel of the user at a predetermined angle, in such a way that the needle can directly push the medicine into the blood vessel of the user, wherein the predetermined angle may be 30 degrees.

As shown in FIG. 6, when in use, the portion of the hydraulic hose, the needle, the portion of the medicine output component, and the blood vessel calibration module 124 and the positioning module 125 are together arranged in a hermetic box. In the box, the needle can be aligned with the blood vessel calibration module 124 by the positioning module 125.

In a specific application, the blood vessel calibration module can be sealing rubber. The blood vessel calibration module is fixed to the body (such as a wrist) of the user so as to ensure that it cannot be moved freely and thereby the needle can be precisely inserted into the blood vessel.

Figure 7:
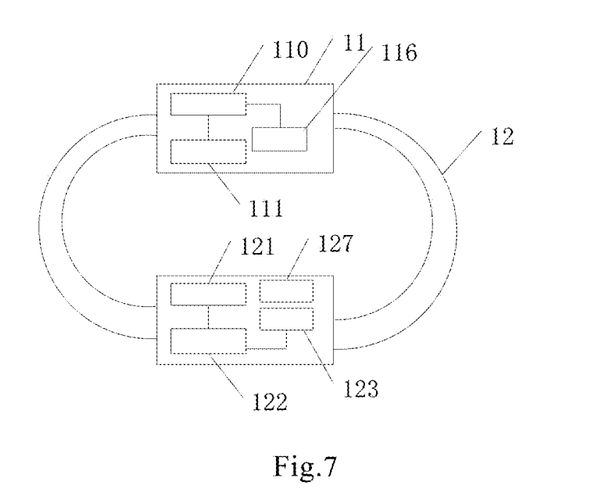
FIG. 7 is a second schematic view of the smart wearable device according to an embodiment.

FIG. 7 is a second schematic view of the smart wearable device according to an embodiment. As shown in FIG. 7, the main body 11 may further comprise a display module 116 configured to display the monitored biological feature parameter. In an embodiment, the display module 116 displays the monitored biological feature parameter under the control of the control unit 110. To be specific, the display module 116 can receive the fifth instruction of the control unit and display the monitored biological feature parameter according to the fifth instruction. The smart device may also be provided with an alarm module 123 for receiving a fourth instruction from the control unit when the control unit determines that the user is in need of first aid according to the comparative result, and sending alarm information according to the fourth instruction. As shown in FIG. 7, the alarm module 123 may be disposed on the connecting part 12. In a specific application, the alarm module 123 may also be arranged on the main body 11. In addition, the connecting part 12 may be provided with a storage module 127 for storing the biological feature reference parameter.

Figure 8:
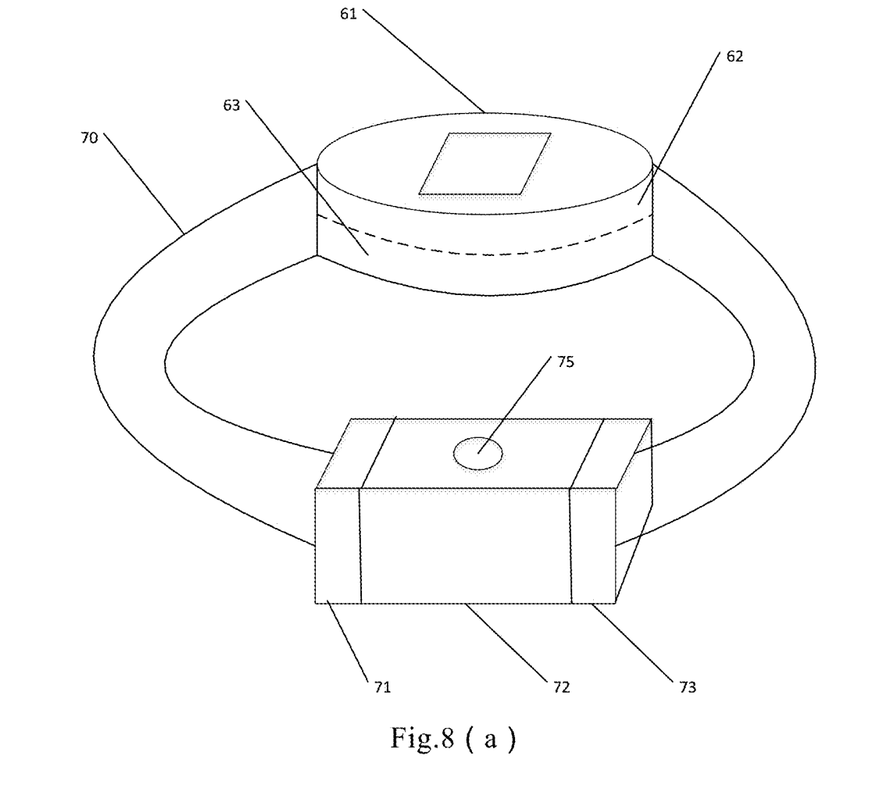
FIG. 8(a) is a schematic view illustrating a specific application of the smart wearable device according to an embodiment.
FIG. 8(b) is a schematic view illustrating an arrangement of a light outlet of a photoelectric sensing measurer according to an embodiment.

FIG. 8(a) is a schematic view illustrating a specific application of the smart wearable device according to an embodiment. FIG. 8(a) illustrates a specific form of the smart wearable device in an actual application. In the smart wearable device as shown in FIG. 8(a), the main body comprises a display screen 61, a control unit 62 and a photoelectrical sensing measurer 63. A light outlet (as shown in FIG. 8(b)) is disposed at a side of the photoelectrical sensing measurer 63 that is close to the skin of the user. The connecting part 70 comprises a battery 71, a hermetic injection cartridge 72 and an alarm unit 73. A needle outlet 75 is disposed at a side of the hermetic injection cartridge 72 that is close to the skin of the user. The hermetic injection cartridge 72 is provided therein with the first-aid processing unit.

As can be seen from the above, when the smart wearable device is powered up, the control unit can determine whether the user is in need of first aid according to the acquired monitored biological feature parameter. If the user needs first aid, the user can be injected with the medicine by the first-aid processing module in the smart wearable device. Thus, the users can be given first aid if they are in need of first aid due to their physical conditions.

Figure 9:
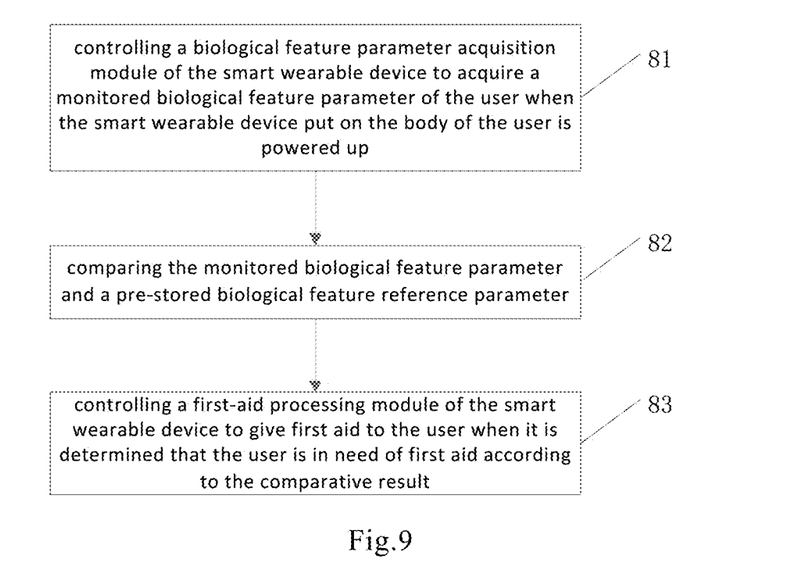
FIG. 9 is a flow chart of a method for implementing first-aid by means of the smart wearable device according to an embodiment.

FIG. 9 is a flow chart of a method for implementing first-aid by means of the smart wearable device according to an embodiment. In some embodiments, the method for implementing first-aid by means of the smart wearable device can be executed by the control unit of the smart wearable device. As shown in FIG. 9, the method comprises the steps of:

Step 81: controlling a biological feature parameter acquisition module of the smart wearable device to acquire a monitored biological feature parameter of the user when the smart wearable device put on the body of the user is powered up. In an embodiment, the step 81 further comprises the step of obtaining the monitored biological feature parameter from the biological feature parameter acquisition module.

Step 82: comparing the monitored biological feature parameter and a pre-stored biological feature reference parameter.

Step 83: controlling a first-aid processing module of the smart wearable device to give first aid to the user when it is determined that the user is in need of first aid according to the comparative result.

In some embodiments, the monitored biological feature parameter includes, but is not limited to, a heart rate of the user.

The Step 83 may also comprise: the control unit controlling a needle push module of the first-aid processing module to push an injection module of the first-aid processing module so that the needle of the injection module pierces into the body of the user. The control can be realized by sending an instruction to the first-aid processing module. In addition, the control unit controls a medicine supply module of the first-aid processing module to push the medicine into the injection module so that the medicine is pushed through the needle into the body of the user.

At the time of controlling a needle push module of the first-aid processing module to push an injection module of the smart device, the control unit sends a first instruction to a first electromagnetic valve of the needle push module, the first electromagnetic valve pushes a first push component of the needle push module according to the first instruction, the first push component acts on a hydraulic component of the needle push module so as to make the hydraulic component to push the injection module.

At the time of controlling a medicine supply module of the first-aid processing module to push the medicine into the injection module, the control unit sends a third instruction to a second electromagnetic valve of the medicine supply module, the second electromagnetic valve pushes a second push component of the medicine supply module according to the third instruction, the second push component pushes the medicine in a medicine storage component of the medicine supply module so that the medicine is pushed through a medicine output component of the medicine supply module into the injection module.

The medicine is pushed through the medicine output component to a medicine input port disposed in the sidewall of the injection module that is close to the medicine supply module, and is pushed through the medicine input port into the injection module.

As can be seen from the above, when the smart wearable device is powered up, the control unit can determine whether the user is in need of first aid according to the acquired monitored biological feature parameter. If the user needs first-aid services, the user can be injected with the medicine by the first-aid processing module in the smart wearable device. Thus, the users can be given first aid if they are in need of first aid due to their physical conditions.

Figure 10:
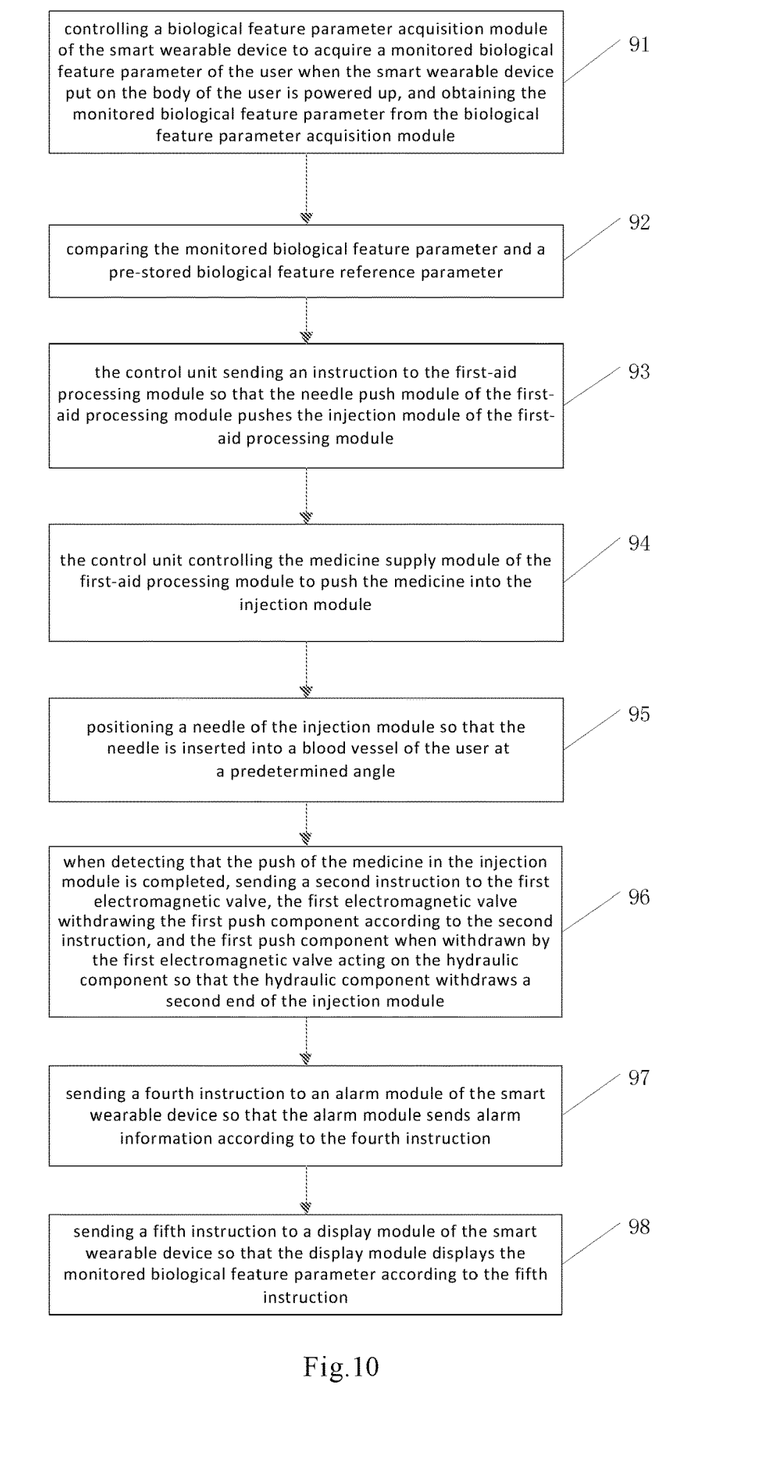
FIG. 10 is a flow chart of a method for implementing first-aid by means of the smart wearable device according to an embodiment.

FIG. 10 is a flow chart of a method for implementing first-aid by means of the smart wearable device according to an embodiment. In some embodiments, the method for implementing first-aid by means of the smart wearable device can be executed by the control unit of the smart wearable device. As shown in FIG. 10, the method comprises the steps of:

Step 91: controlling a biological feature parameter acquisition module of the smart wearable device to acquire a monitored biological feature parameter of the user when the smart wearable device put on the body of the user is powered up, and obtaining the monitored biological feature parameter from the biological feature parameter acquisition module.

Step 92: comparing the monitored biological feature parameter and a pre-stored biological feature reference parameter.

Step 93: the control unit sending an instruction to the first-aid processing module so that the needle push module of the first-aid processing module pushes the injection module of the first-aid processing module.

Step 94: the control unit controlling the medicine supply module of the first-aid processing module to push the medicine into the injection module.

Step 95: positioning a needle of the injection module so that the needle is inserted into a blood vessel of the user at a predetermined angle.

Step 96: when detecting that the push of the medicine in the injection module is completed, sending a second instruction to the first electromagnetic valve, the first electromagnetic valve withdrawing the first push component according to the second instruction, and the first push component when withdrawn by the first electromagnetic valve acting on the hydraulic component so that the hydraulic component withdraws a second end of the injection module.

Step 97: sending a fourth instruction to an alarm module of the smart wearable device so that the alarm module sends alarm information according to the fourth instruction, also referred to as an alarm instruction.

Step 98: sending a fifth instruction to a display module of the smart wearable device so that the display module displays the monitored biological feature parameter according to the fifth instruction.

In different embodiments, one of steps 97 and 98 or the combination thereof will be executed.

It shall be pointed out that the above method can be realized by a computer executable instruction stored on the computer readable storage medium. When the executable instruction is executed by one or more processors, the executable instruction causes the one or more processors to implement any one of the above methods. In an embodiment, the executable instruction can be executed by the control unit so that the control unit can be caused to execute any one of the above methods.

As can be seen from the above, when the smart wearable device is powered up, the control unit can determine whether the user is in need of first aid according to the acquired monitored biological feature parameter. If the user needs first-aid services, the user can be injected with the medicine by the first-aid processing module in the smart wearable device. Thus, the users can be given first aid if they are in need of first aid due to their physical conditions.

It can be understood that the above embodiments are only exemplary embodiments of the present invention, but the protection scope of the present invention is not limited thereto. It shall be pointed out that those skilled in the art can readily conceive of various variations or replacements without departing from the spirit and scope of the present invention. These variations or replacements will fall within the protection scope of the present invention. Thus, the protection scope of the present invention shall be based on the protection scope of the appended claims.

What needs to be explained is that some of the above embodiments are only illustrated by way of the individual function modules division. In actual application, the above functions can be allocated to different functional modules as desired. The internal structure of the device can be divided into different functional modules so as to accomplish all or part of the functions as stated above. In addition, function(s) of the above one module can be achieved by a plurality of modules, and functions of the plurality of modules can be integrated into one module.

The term "and/or" used herein is only used to describe the connecting relations between objects connected thereby, which may be of three types. For instance, "A and/or B" can represent the following three situations: either A alone, or B alone, or both A and B. In addition, the character "/" used herein generally indicates that the former and the latter objects connected thereby is in a "or" relationship.

The present application uses such wordings as "first", "second" and "third". Unless specified in the context, such wordings do not imply any order, but are actually used for the purpose of identification. For instance, the phrases "a first instruction" and "a second instruction" do not necessarily mean the first instruction is generated, sent or executed earlier than the second instruction. In fact, these phrases are only used to identify different instructions.

In the claims, any reference sign in parentheses should not be interpreted as a limitation to the claims. The term "comprise/include" does not exclude the presence of elements or steps other than those listed in the claims. The word "a" or "an" in front of elements do not exclude the presence of a plurality of such elements. The present invention may be achieved by hardware comprising a plurality of separate elements, or by properly programmed software or firmware, or by any combination thereof.

In device or system claims that enumerate several means, one or more of the means can be embodied in one and the same item of hardware. The mere fact that some measures are recited in dependent claims that are different from each other does not indicate that the combination of the measures cannot be used to advantage.

What is claimed is:

1. A smart wearable device, comprising:
a main body comprising a control unit and a biological feature parameter acquisition module, the biological feature parameter acquisition module being configured to acquire a monitored biological feature parameter of a user, and the control unit being configured to compare the monitored biological feature parameter and a pre-stored biological feature reference parameter so as to determine whether the user is in need of first aid according to the comparative result;

a connecting part for putting on the smart wearable device on the body of the user;

a power supply module for supplying power to the smart wearable device; and a first-aid processing module configured to give first aid to the user when it is determined according to the comparative result that the user is in need of first aid.

2. The smart wearable device according to claim 1, wherein the first-aid processing module comprises an injection module, a needle push module and a medicine supply module, the injection module is provided at a first end with a needle and is connected at a second end with the needle push module, when it is determined that the user is in need of first aid according to the comparative result, the control unit controls the needle push module to push the second end of the injection module so as to make the needle pierce the body of the user, and controls the medicine supply module to push the medicine into the injection module during the control of the needle push module, in such a way that the medicine is pushed into the body of the user through the needle.

3. The smart wearable device according to claim 2, wherein the needle push module comprises a first electromagnetic valve, a first push component and a hydraulic component having a cavity, the first end of the first push component is connected with the first electromagnetic valve, and the second end of the first push component is movably disposed in the first end of the cavity of the hydraulic component, the second end of the injection module is movably disposed in the second end of the cavity of the hydraulic component, the control unit sends a first instruction to the first electromagnetic valve; the first electromagnetic valve pushes the first push component according to the first instruction of the control unit, and the first push component when pushed by the first electromagnetic valve acts on the hydraulic component so that the hydraulic component pushes the second end of the injection module.

4. The smart wearable device according to claim 3, wherein when the control unit detects that the push of the medicine in the injection module is completed, the control unit sends a second instruction to the first electromagnetic valve, the first electromagnetic valve withdraws the first push component according to the second instruction of the control unit, and the first push component when withdrawn by the first electromagnetic valve acts on the hydraulic component, so that the hydraulic component withdraws the injection module.

5. The smart wearable device according to claim 3, wherein the cavity of the hydraulic component is L-shaped or U-shaped.

6. The smart wearable device according to claim 2, wherein the injection module further comprises a sealing module for sealing the end of the needle to be pierced into the body of the user.

7. The smart wearable device according to claim 2, wherein the medicine supply module comprises a second electromagnetic valve, a second push component, a medicine storage component and a medicine output component, the control unit sends a third instruction to the second electromagnetic valve, the second electromagnetic valve pushes the second push component according to the third instruction of the control unit, so that the second push component pushes the medicine in the medicine storage component and the medicine is pushed through the medicine output component into the injection module.

8. The smart wearable device according to claim 7, wherein the injection module is a hollow cylinder, and a medicine input port is disposed in the sidewall of the injection module that is close to the medicine supply module; the medicine is pushed through the medicine output component into the medicine input port and then pushed through the medicine input port into the injection module.

9. The smart wearable device according to claim 7, wherein the medicine output component is a flexible tube.

10. The smart wearable device according to claim 2, wherein the smart wearable device further comprises:

a blood vessel calibration module adhered to the body of the user and aligned with the blood vessel of the user;

a positioning module for aligning the needle of the injection module with the blood vessel calibration module so as to insert the needle into the blood vessel of the user at a predetermined angle.

11. The smart wearable device according to claim 1, wherein the monitored biological feature parameter comprises a heart rate of the user.

12. A method for implementing first-aid by means of a smart wearable device, comprising the steps of:

controlling a biological feature parameter acquisition module of the smart wearable device to acquire a monitored biological feature parameter of the user when the smart wearable device put on the body of the user is powered up;

comparing the monitored biological feature parameter and a pre-stored biological feature reference parameter; and controlling a first-aid processing module of the smart wearable device to give first aid to the user when it is determined that the user is in need of first aid according to the comparative result.

13. The method according to claim 12, wherein the step of controlling a first-aid processing module of the smart wearable device to give first aid to the user when it is determined that the user is in need of first aid according to the comparative result further comprises the steps of:

controlling a needle push module of the first-aid processing module to push an injection module of the first-aid processing module so that the needle of the injection module pierces into the body of the user; and controlling a medicine supply module of the first-aid processing module to push the medicine into the injection module so that the medicine is pushed through the needle into the body of the user.

14. The method according to claim 13, wherein the step of controlling a needle push module of the first-aid processing module to push an injection module of the smart device comprises the step of:

sending a first instruction to a first electromagnetic valve of the needle push module, the first electromagnetic valve pushing a first push component of the needle push module according to the first instruction, the first push component acting on a hydraulic component of the needle push module so as to make the hydraulic component to push the injection module to move.

15. The method according to claim 13, wherein the step of controlling a medicine supply module of the first-aid processing module to push the medicine into the injection module comprises the step of:

sending a third instruction to a second electromagnetic valve of the medicine supply module, the second electromagnetic valve pushing a second push component of the medicine supply module according to the third instruction, the second push component pushing the medicine in a medicine storage component of the medicine supply module so that the medicine is pushed through a medicine output component of the medicine supply module into the injection module.

16. The method according to claim 15, wherein the medicine is pushed through the medicine output component to a medicine input port disposed in the sidewall of the injection module that is close to the medicine supply module, and is pushed through the medicine input port into the injection module.

17. The method according to claim 13, wherein the step of controlling a needle push module of the first-aid processing module to push an injection module of the first-aid processing module further comprises the step of:

positioning a needle of the injection module so that the needle is inserted into a blood vessel of the user at a predetermined angle.

18. The method according to claim 14, wherein the method further comprises the step of:

when detecting that the push of the medicine in the injection module is completed, sending a second instruction to the first electromagnetic valve, the first electromagnetic valve withdrawing the first push component according to the second instruction, and the first push component when withdrawn by the first electromagnetic valve acting on the hydraulic component so that the hydraulic component withdraws a second end of the injection module.

19. The method according to claim 12, wherein the monitored biological feature parameter comprises a heart rate of the user.

20. A computer readable storage medium containing computer executable instructions which, when executed by one or more processors, cause the one or more processors to execute the method according to claim 12.

* * * * *